(12) United States Patent
Mu et al.

(10) Patent No.: US 12,251,413 B2
(45) Date of Patent: Mar. 18, 2025

(54) **USE OF EFFECTIVE PART EXTRACT OF *MONOCHASMA SAVATIERI* IN PREPARATION OF DRUG FOR TREATING INFLAMMATORY DISEASE OR TUMOR**

(71) Applicants: Harbin Kanglong Pharmaceutical Co., Ltd., Harbin (CN); Yichun Bingchen Ag. Tech. Dev. Co., Ltd., Yichun (CN)

(72) Inventors: Bin Mu, Harbin (CN); Jiangong Shi, Harbin (CN); Tiantai Zhang, Harbin (CN); Qinglan Guo, Harbin (CN); Weiquan Li, Harbin (CN)

(73) Assignees: HARBIN KANGLONG PHARMACEUTICAL CO., LTD, Heilongjiang Province (CN); YICHUN BINGCHEN AGRICULTURAL TECHNOLOGY DEVELOPMENT CO., LTD., Jiangxi Province (CN)

( * ) Notice: Subject to any disclaimer, the term of this patent is extended or adjusted under 35 U.S.C. 154(b) by 0 days.

(21) Appl. No.: 17/903,026

(22) Filed: Sep. 5, 2022

(65) Prior Publication Data
US 2023/0398168 A1 Dec. 14, 2023

(30) Foreign Application Priority Data
Jun. 14, 2022 (CN) .......................... 202210673135.9

(51) Int. Cl.
*A61K 36/64* (2006.01)
*A61P 1/00* (2006.01)
(Continued)

(52) U.S. Cl.
CPC ................ *A61K 36/64* (2013.01); *A61P 1/00* (2018.01); *A61P 17/06* (2018.01); *A61P 19/02* (2018.01);
(Continued)

(58) Field of Classification Search
CPC ................ A61K 36/64; A61K 2236/39; A61K 2236/331; A61P 29/00; A61P 31/00; A61P 1/00; A61P 19/02; A61P 17/06
See application file for complete search history.

(56) References Cited

FOREIGN PATENT DOCUMENTS

CN 103387912 A 11/2013

OTHER PUBLICATIONS

Heinrich et al.; "Best Practice in the chemical characterization of extracts used in pharmacological and toxicological research—The ConPhyMP-Guidelines"; 2022; Frontiers in Pharmacology; DOI 10.3389/fphar.2022.953205 (Year: 2022).*

(Continued)

*Primary Examiner* — Timothy P Thomas
(74) *Attorney, Agent, or Firm* — PATENT-ARTS; Gerard H. Bencen, Esq.

(57) ABSTRACT

The present disclosure provides use of an effective part extract of *Monochasma savatieri* in preparation of a drug for treating an inflammatory disease or a tumor. In the present disclosure, an effective part of *Monochasma savatieri* is separated and purified by various separation and purification methods (including solvent extraction, macroporous resin column chromatography, MCI column separation, and Sephadex LH-20 gel column separation) separately, to obtain the effective part extract of *Monochasma savatieri*. The effective part extract of *Monochasma savatieri* is capable of significantly inhibiting secretion of TNF-α, and significantly inhibiting proliferation of breast cancer cells and lung cancer cells, thereby effectively treating the inflammatory disease or the tumor. The present disclosure provides a favorable theoretical basis for finding a drug that can effectively treat the inflammatory disease or the tumor from the *Monochasma savatieri*, which is of great significance to development of novel drugs.

3 Claims, 1 Drawing Sheet

(51) Int. Cl.
*A61P 17/06* (2006.01)
*A61P 19/02* (2006.01)
*A61P 29/00* (2006.01)
*A61P 31/00* (2006.01)
*A61P 35/00* (2006.01)

(52) U.S. Cl.
CPC ............... *A61P 29/00* (2018.01); *A61P 31/00* (2018.01); *A61P 35/00* (2018.01); *A61K 2236/331* (2013.01); *A61K 2236/39* (2013.01)

(56) References Cited

OTHER PUBLICATIONS

Gao et al.; "Isoacteoside, a dihydroxyphenylethyl glycoside, exhibits anti-inflammatory effects through blocking toll-like receptor 4 dimerization"; 2017; British Journal of Pharmacology; 174; 2880-2896; DOI:10.1111/bph.13912 (Year: 2017).*
"Deer Antler Grass Wine Service Prescription", "Dictionary of Arsunoma Prescriptions", edited by Zhao Jiancheng, etc., Traditional Chinese Medicine Ancient Books Publishing House, No. 584 page, open date Apr. 30, 2009). google translate AND Original Chinese Document, cited in CN.

* cited by examiner

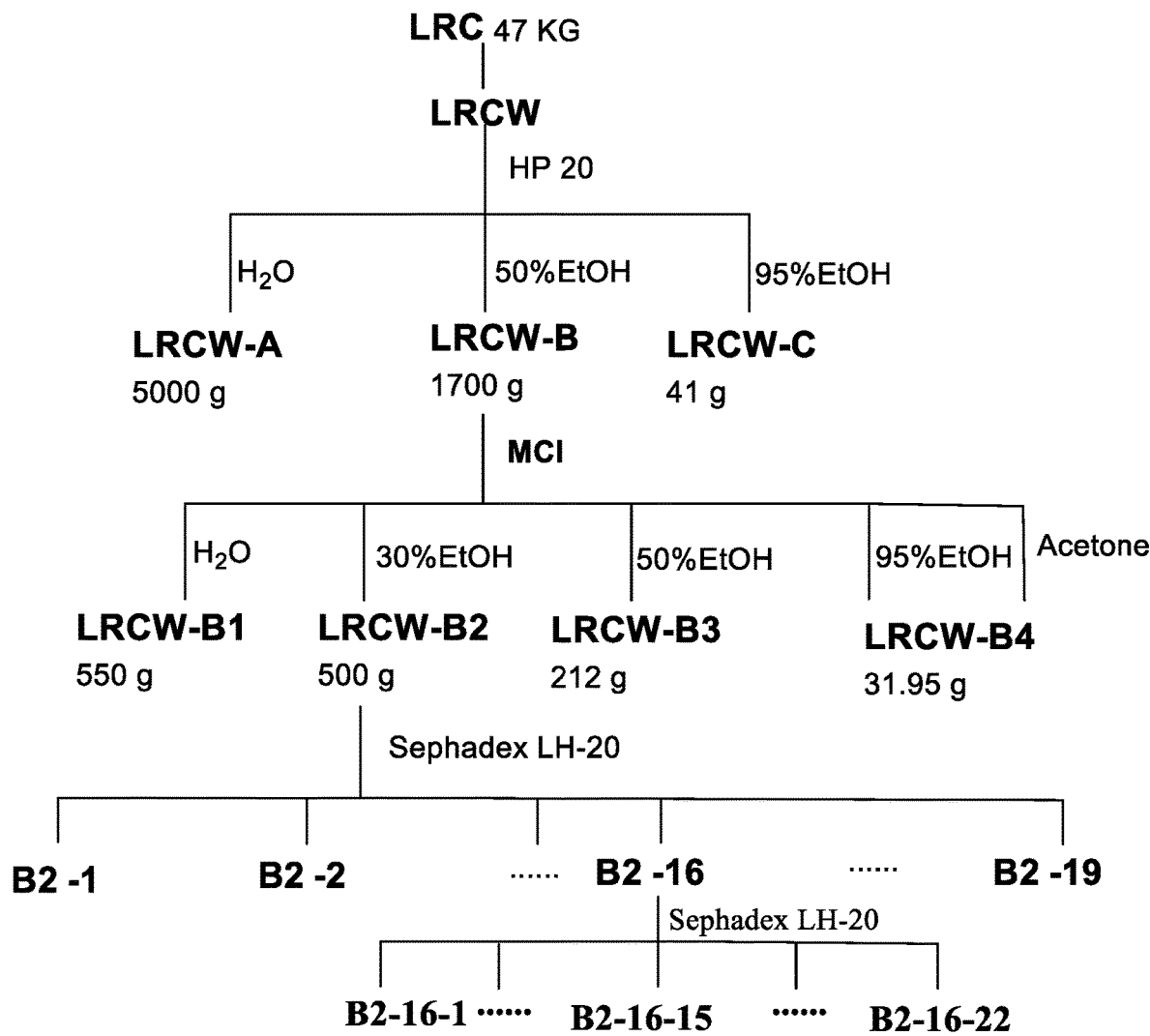

USE OF EFFECTIVE PART EXTRACT OF *MONOCHASMA SAVATIERI* IN PREPARATION OF DRUG FOR TREATING INFLAMMATORY DISEASE OR TUMOR

CROSS REFERENCE TO RELATED APPLICATION

This patent application claims the benefit and priority of Chinese Patent Application No. 202210673135.9, filed on Jun. 14, 2022, the disclosure of which is incorporated by reference herein in its entirety as part of the present application.

TECHNICAL FIELD

The present disclosure belongs to the technical field of traditional Chinese medicine extracts, and in particular relates to use of an effective part extract of *Monochasma savatieri* in preparation of a drug for treating an inflammatory disease or a tumor.

BACKGROUND ART

Inflammation is a part of normal biological responses to noxious stimuli such as tissue damage, pathogens, and irritants; chronic inflammation may develop due to persistent stimuli (such as irritants or pathogens) or due to abnormal immune system function (such as autoimmune inflammatory diseases). TNF-α inhibitors are also the first choice for the treatment of autoimmune inflammatory diseases, including rheumatoid arthritis (RA), ankylosing spondylitis (AS), and psoriatic arthritis (PsA). However, current TNF-α inhibitors are not effective in the treatment of autoimmune inflammatory diseases. For example, even if an initial bioavailability of infliximab approaches 100% due to intravenous administration of a drug, differences in pharmacokinetics may lead to individual patients having insufficient drug levels for extended periods of time between infusions, resulting in failure to respond. In addition, malignant tumors have seriously affected the overall health level and quality of life of the whole people. Since there is no efficient and safe drug to treat tumors, the malignant tumors have an annually increasing mortality rate, becoming the second leading cause of human death. Studies have shown that many natural plant extracts have desirable anti-tumor and anti-inflammatory activities. Therefore, it has become an effective way to study anti-inflammatory and anti-tumor drugs by finding drugs from Chinese herbal medicines.

*Monochasma savatieri* Franch. is a plant of the genus *Monochasma* in the family Scrophulariaceae. The *Monochasma savatieri* can be used as a drug with whole herb, with functions of clearing away heat and detoxification, cooling blood and hemostasis, and dispelling dampness and relieving pain. The *Monochasma savatieri* is mainly used for treating diseases including colds, pneumonia, fever, cough, hematemesis, red dysentery, hematochezia, irregular menstruation, rheumatism, bone pain, toothache, and acute mastitis. However, relatively few researches have been done on the chemical composition of *Monochasma savatieri*. So far, from acetone, water, or ethanol extracts of the *Monochasma savatieri*, only more than 30 compounds of structural types have been reported, including phenethyl glycosides, iridoid glycosides, flavones, and organic acids.

SUMMARY

In view of this, an objective of the present disclosure is to provide use of an effective part extract of *Monochasma savatieri* in preparation of a drug for treating an inflammatory disease or a tumor. The effective part extract of *Monochasma savatieri* can effectively treat the inflammatory disease or the tumor.

To achieve the above objective, the present disclosure provides the following technical solutions.

The present disclosure provides use of an effective part extract of *Monochasma savatieri* in preparation of a drug for treating a tumor, where the effective part extract of *Monochasma savatieri* includes one or two of a water elution fraction LRCW-A and a 40% to 60% ethanol elution fraction LRCW-B that are separated by macroporous resin from a *Monochasma savatieri* crude extract; and a preparation method of the LRCW-A and the LRCW-B includes the following steps:

(1) pulverizing the *Monochasma savatieri*, mixing with water, conducting extraction 2 to 4 times by decoction for 20 min to 40 min each time, combining filtrates, and conducting vacuum concentration on a combined filtrate to obtain the *Monochasma savatieri* crude extract; and (2) separating the *Monochasma savatieri* crude extract by an HP-20 macroporous resin column chromatography, and conducting elution with 150 L to 250 L of water and 150 L to 250 L of 40% to 60% ethanol in sequence, to obtain the LRCW-A and the LRCW-B, respectively.

Preferably, the effective part extract of *Monochasma savatieri* may include one or more of LRCW-B1, LRCW-B2, LRCW-B3, and LRCW-B4; and a preparation method of the LRCW-B1, the LRCW-B2, the LRCW-B3, and the LRCW-B4 may include the following steps:

separating the LRCW-B by an MCI column chromatography, and conducting elution with 35 L to 45 L of water, 35 L to 45 L of 25% to 35% ethanol, 35 L to 45 L of 40% to 60% ethanol, and 35 L to 45 L of 80% to 95% ethanol, to obtain the LRCW-B1, the LRCW-B2, the LRCW-B3, and the LRCW-B4, respectively.

Preferably, the effective part extract of *Monochasma savatieri* may include one or more of B2-2, B2-3, B2-6, B2-10, B2-11, B2-12, B2-13, B2-14, B2-15, B2-16, B2-17, and B2-18; and a preparation method of B2-1 to B2-19 may include the following steps:

separating the LRCW-B2 by a Sephadex LH-20 gel column chromatography, and conducting gradient elution with absolute ethanol and water in a volume ratio of 1:0 to 0:1 as a mobile phase; and combining same fractions according to results of thin layer chromatography to obtain the B2-1 to the B2-19.

Preferably, the effective part extract of *Monochasma savatieri* may include one or more of B2-16-1, B2-16-3, B2-16-4, B2-16-5, B2-16-6, B2-16-18, B2-16-19, B2-16-20, B2-16-21, and B2-16-22; and a preparation method of the B2-16-1 to the B2-16-22 may include the following steps:

separating the B2-16 by the Sephadex LH-20 gel column chromatography, and conducting gradient elution with absolute ethanol and water in a volume ratio of 1:0 to 0:1 as a mobile phase; and combining same fractions according to results of thin layer chromatography to obtain the B2-16-1 to the B2-16-22.

Preferably, the tumor may include one or two of breast cancer and lung cancer.

Preferably, when the tumor is lung cancer, the effective part extract of *Monochasma savatieri* may include one or more of the B2-2, the B2-3, the B2-6, the B2-16-1, the B2-16-3, and the B2-16-4.

The present disclosure provides use of an effective part extract of *Monochasma savatieri* in preparation of a drug for treating an inflammatory disease, where the effective part extract of *Monochasma savatieri* includes one or more of the B2-13, the B2-15, the B2-16, and the B2-16-15.

Preferably, the drug may be capable of significantly inhibiting secretion of an inflammatory factor TNF-α.

Preferably, the inflammatory disease may include sepsis, inflammatory bowel disease, rheumatoid arthritis, ankylosing spondylitis, or psoriasis.

Preferably, the drug may include the effective part extract of *Monochasma savatieri* as an active ingredient and a pharmaceutically acceptable carrier or auxiliary material.

Compared with the prior art, the present disclosure has the following beneficial effects.

The present disclosure provides use of an effective part extract of *Monochasma savatieri* in preparation of a drug for treating an inflammatory disease or a tumor. In the present disclosure, an effective part of *Monochasma savatieri* is separated and purified by various separation and purification methods (including solvent extraction, macroporous resin column chromatography, MCI column separation, and Sephadex LH-20 gel column separation) separately, to obtain the effective part extract of *Monochasma savatieri*. The effective part extract of *Monochasma savatieri* is capable of significantly inhibiting secretion of TNF-α, and significantly inhibiting proliferation of breast cancer cells and lung cancer cells, thereby effectively treating the inflammatory disease or the tumor. The present disclosure provides a favorable theoretical basis for finding a drug that can effectively treat the inflammatory disease or the tumor from the *Monochasma savatieri*, which is of great significance to development of novel drugs.

BRIEF DESCRIPTION OF THE DRAWINGS

FIG. 1 shows a preparation flow chart of an effective part extract of *Monochasma savatieri*.

DETAILED DESCRIPTION OF THE EMBODIMENTS

The present disclosure provides use of an effective part extract of *Monochasma savatieri* in preparation of a drug for treating a tumor, where the effective part extract of *Monochasma savatieri* includes one or two of a water elution fraction LRCW-A and a 40% to 60% ethanol elution fraction LRCW-B that are separated by macroporous resin from a *Monochasma savatieri* crude extract; and a preparation method of the LRCW-A and the LRCW-B includes the following steps:

(1) pulverizing the *Monochasma savatieri*, mixing with water, conducting extraction 2 to 4 times by decoction for 20 min to 40 min each time, combining filtrates, and conducting vacuum concentration on a combined filtrate to obtain the *Monochasma savatieri* crude extract; and (2) separating the *Monochasma savatieri* crude extract by an HP-20 macroporous resin column chromatography, and conducting elution with 150 L to 250 L of water and 150 L to 250 L of 40% to 60% ethanol in sequence, to obtain the LRCW-A and the LRCW-B, respectively.

In the present disclosure, the *Monochasma savatieri* is pulverized, mixed with water, extraction is conducted 2 to 4 times by decoction, filtrates are combined, and vacuum concentration is conducted on the combined filtrate to obtain the *Monochasma savatieri* crude extract. The *Monochasma savatieri* is pulverized to a length of preferably 3 cm to 5 cm; and the *Monochasma savatieri* and water have a mass-volume ratio of preferably 1 g:(4-8) mL, more preferably 1 g:(5-7) mL. After the raw material pulverization and material-liquid ratio setting, a release rate and a release amount of the active ingredients are improved, thereby reducing the amount of raw materials and saving an extraction time. In order to ensure a medicinal effect of the *Monochasma savatieri* crude extract, each extraction is conducted for preferably 25 min to 35 min, which significantly improves an active ingredient content of the *Monochasma savatieri* crude extract. The filtrate is subjected to vacuum concentration to obtain an extract.

In the present disclosure, the effective part extract of *Monochasma savatieri* includes one or more of LRCW-B1, LRCW-B2, LRCW-B3, and LRCW-B4; and a preparation method of the LRCW-B1, the LRCW-B2, the LRCW-B3, and the LRCW-B4 includes the following steps:

separating the LRCW-B by an MCI column chromatography, and conducting elution with L to 45 L of water, 35 L to 45 L of 25% to 35% ethanol, 35 L to 45 L of 40% to 60% ethanol, and 35 L to 45 L of 80% to 95% ethanol, to obtain the LRCW-B1, the LRCW-B2, the LRCW-B3, and the LRCW-B4, respectively.

In the present disclosure, the effective part extract of *Monochasma savatieri* includes one or more of B2-2, B2-3, B2-6, B2-10, B2-11, B2-12, B2-13, B2-14, B2-15, B2-16, B2-17, and B2-18; and a preparation method of B2-1 to B2-19 includes the following steps:

separating the LRCW-B2 by a Sephadex LH-20 gel column chromatography, and conducting gradient elution with absolute ethanol and water in a volume ratio of 1:0 to 0:1 as a mobile phase; and combining same fractions according to results of thin layer chromatography to obtain the B2-1 to the B2-19.

In the present disclosure, the effective part extract of *Monochasma savatieri* includes one or more of B2-16-1, B2-16-3, B2-16-4, B2-16-5, B2-16-6, B2-16-18, B2-16-19, B2-16-20, B2-16-21, and B2-16-22; and a preparation method of the B2-16-1 to the B2-16-22 includes the following steps:

separating the B2-16 by the Sephadex LH-20 gel column chromatography, and conducting gradient elution with absolute ethanol and water in a volume ratio of 1:0 to 0:1 as a mobile phase; and combining same fractions according to results of thin layer chromatography to obtain the B2-16-1 to the B2-16-22.

In the present disclosure, the tumor includes preferably one or two of breast cancer and lung cancer; as a preferred example, when the tumor is lung cancer, the effective part extract of *Monochasma savatieri* includes one or more of the B2-2, the B2-3, the B2-6, the B2-16-1, the B2-16-3, and the B2-16-4.

The present disclosure provides use of an effective part extract of *Monochasma savatieri* in preparation of a drug for treating an inflammatory disease, where the effective part extract of *Monochasma savatieri* includes one or more of the B2-13, the B2-15, the B2-16, and the B2-16-15.

In the present disclosure, an activity evaluation of a series of fractions is conducted through an inflammatory factor TNF-α inhibition experiment and a tumor cell proliferation inhibition experiment; results show that the fractions B2-13, B2-15, B2-16, and B2-16-15 can significantly inhibit the secretion of TNF-α; the fractions LRCW-A, LRCW-B1 to LRCW-B4, B2-3, B2-6, B2-10 to B2-18, B2-16-1, B2-16-3 to B2-16-6, and B2-16-18 to B2-16-22 can inhibit the proliferation of breast cancer cell MCF-7; and the fractions B2-2, B2-3, B2-6, B2-16-1, B2-16-3, and B2-16-4 can inhibit the proliferation of lung cancer cell A549.

In the present disclosure, the drug is capable of significantly inhibiting secretion of an inflammatory factor TNF-α. The inflammatory disease includes sepsis, inflammatory bowel disease, rheumatoid arthritis, ankylosing spondylitis, or psoriasis.

In the present disclosure, the *Monochasma savatieri* Franch. is a plant of the genus *Monochasma* in the family Scrophulariaceae, and the *Monochasma savatieri* can be used as a drug with whole herb.

In the present disclosure, the drug includes the effective part extract of *Monochasma savatieri* as an active ingredient and a pharmaceutically acceptable carrier or auxiliary material; the drug can be prepared according to methods known in the art. For this purpose, if desired, the drug may be combined with one or more solid or liquid pharmaceutical excipients and/or auxiliary materials into a suitable administration or dosage form for use as a human or veterinary drug form.

In the present disclosure, the drug can be administered in a unit dosage form through an enteral or parenteral way, such as oral, intramuscular, subcutaneous, nasal, oral mucosa, skin, peritoneal or rectal ways, preferably the oral way. The drug can be administered by injection, including intravenous injection, intramuscular injection, subcutaneous injection, and intradermal injection.

In the present disclosure, a dosage form of the drug can be a liquid dosage form or a solid dosage form; for example, the liquid dosage form includes true solutions, colloids, particulate dosage forms, emulsion dosage forms, or suspension dosage forms; the solid dosage form includes powders, granules, tablets, capsules, dropping pills, pills, powders, freeze-dried powder injections, or films. The drug can also be other dosage forms, such as aerosols, solutions, suspensions, emulsions, or suppositories.

In the present disclosure, the drug can be prepared into ordinary preparations, sustained-release preparations, controlled-release preparations, targeted preparations, and various microparticle drug delivery systems.

In the present disclosure, when the dosage form of the drug is a tablet, the carrier may be a diluent and an absorbent, such as starch, dextrin, calcium sulfate, lactose, mannitol, sucrose, sodium chloride, glucose, urea, calcium carbonate, porcellanite, microcrystalline cellulose, aluminum silicate, and the like; a humectant and a binder, such as water, glycerol, polyethylene glycol, ethanol, propanol, starch slurry, dextrin, syrup, honey, glucose solution, *mucilago acaciae*, gelatin slurry, sodium carboxymethylcellulose, lac, methylcellulose, potassium phosphate, polyvinylpyrrolidone, and the like; a disintegrating agent, such as dried starch, alginate, agar powder, laminaran, sodium bicarbonate and citric acid, calcium carbonate, polyoxyethylene, sorbitol fatty acid ester, sodium dodecyl sulfate, methyl cellulose, ethyl cellulose, and the like; a disintegration inhibitor, such as sucrose, glyceryl tristearate, cocoa butter, hydrogenated oil, and the like; an absorption promoter, such as a quaternary ammonium salt, sodium dodecyl sulfate, and the like; and a lubricant, such as talc, silica, corn starch, stearate, boric acid, liquid paraffin, polyethylene glycol, and the like. The tablet can also be further made into a coated tablet, such as a sugar-coated tablet, a film-coated tablet, an enteric coated tablet, or a double-layer tablet and a multi-layer tablet.

In the present disclosure, when the dosage form of the drug is a pill, the carrier may be a diluent and an absorbent, such as glucose, lactose, starch, cocoa butter, hydrogenated vegetable oil, polyvinylpyrrolidone, Gelucire, kaolin, talc, and the like; a binder, such as Arabic gum, tragacanth gum, gelatin, ethanol, honey, liquid sugar, rice paste or panada, and the like; a disintegrating agent, such as agar powder, dried starch, alginate, sodium dodecyl sulfate, methyl cellulose, ethyl cellulose, and the like.

In the present disclosure, when the dosage form of the drug is a capsule, the effective part extract of *Monochasma savatieri* is mixed with the above various carriers, and an obtained mixture is placed in a hard gelatin capsule or a soft capsule. The effective part extract of *Monochasma savatieri* can also be prepared into microcapsules, suspended in an aqueous medium to form a suspension, and can also be loaded into hard capsules or prepared into injections for use.

In the present disclosure, when the drug is prepared into an injection preparation, such as solutions, suspension solutions, emulsions, and freeze-dried powder injections, such preparations may be aqueous or non-aqueous, and may include one and/or more pharmaceutically acceptable carriers, diluents, binders, lubricants, preservatives, surfactants, or dispersants. For example, the diluent can be selected from the group consisting of water, ethanol, polyethylene glycol, 1,3-propanediol, ethoxylated isostearyl alcohol, polyoxidized isostearyl alcohol, polyoxyethylene sorbitan fatty acid ester, and the like. Furthermore, in order to prepare an isotonic injection, an appropriate amount of sodium chloride, glucose or glycerin can be added into the injection preparation, and moreover, a conventional cosolvent, a conventional buffer, a conventional pH regulator, and the like may also be added. Furthermore, a colorant, a preservative, a perfume, a flavoring agent, a sweetener or other materials can also be added into the pharmaceutical preparation if desired.

In the present disclosure, the dosage of the drug depends on many factors, including the nature and severity of a disease to be prevented or treated, the sex, age, body weight, personality and individual response of a patient or animal, as well as the route of administration, the number of times of administration, and the treatment purpose. Thus, the therapeutic dosage can vary widely. In general, the dosage of the drug is well known to those skilled in the art. Appropriate adjustments can be made according to an actual amount of the drug contained in the pharmaceutical preparation, to meet the requirements of its therapeutically effective amount and achieve the purpose of prevention or treatment. The drug has a daily dosage of 0.001 mg/kg body weight to 150 mg/kg body weight, preferably 0.01 mg/kg body weight to 100 mg/kg body weight, more preferably 0.01 mg/kg body weight to 60 mg/kg body weight, and most preferably 0.1 mg/kg body weight to 10 mg/kg body weight. The above dosages may be administered in a single dosage or divided into several, such as two, three or four dosages, which is subjected to a clinical experience of administering physicians and a dosing regimen including use of other therapeutic approaches.

The total dosage required for each treatment may be administered in divided or single dosages. The drug can be taken alone or combined with other therapeutic drugs or symptomatic drugs with an adjusted dosage.

The technical solution provided by the present disclosure will be described in detail below with reference to examples, but they should not be construed as limiting the protection scope of the present disclosure.

Example 1

A preparation method of an effective part extract of *Monochasma savatieri* included the following steps:
(1) 47 kg of a *Monochasma savatieri* whole herb was pulverized to a length of 4 cm, mixed with 300 L of water, extraction was conducted 3 times by decoction for 30 min each time, filtrates were combined, and vacuum concentration was conducted on a combined filtrate to obtain an extract, namely 7.68 kg of a *Monochasma savatieri* crude extract;
(2) the *Monochasma savatieri* crude extract was separated by an HP-20 macroporous resin column chromatography, and eluted with 200 L of each of water, 50% ethanol, and 95% ethanol in sequence, to obtain 5,000 g of a water elution fraction (LRCW-A), 1,700 g of a 50% ethanol elution fraction (LRCW-B), and 41 g of a 95% ethanol elution fraction (LRCW-C), respectively;
(3) the LRCW-B was separated by an MCI column chromatography, and eluted with 40 L of each of water, 30% ethanol, 50% ethanol, and 95% ethanol in sequence, to obtain 550 g of LRCW-B1, 500 g of LRCW-B2, 212 g of LRCW-B3, and 31.95 g of LRCW-B4;
(4) the LRCW-B2 was separated by a Sephadex LH-20 gel column chromatography, and gradient elution was conducted with absolute ethanol and water in a volume ratio of 1:0 to 0:1 as a mobile phase; and same fractions were combined according to results of thin layer chromatography to obtain B2-1 to B2-19, with masses of 11.82 g, 62.38 g, 32.07 g, 33.28 g, 55.88 g, 52.65 g, 18.94 g, 12.13 g, 7.19 g, 4.60 g, 7.07 g, 4.60 g, 4.99 g, 63.79 g, 2.77 g, 58.77 g, 27.87 g, 19.84 g, and 2.11 g, respectively; and
(5) the B2-16 was separated by the Sephadex LH-20 gel column chromatography, and gradient elution was conducted with absolute ethanol and water in a volume ratio of 1:0 to 0:1 as a mobile phase; and same fractions were combined according to results of thin layer chromatography to obtain B2-16-1 to B2-16-22, with masses of 0.21 g, 1.24 g, 0.49 g, 0.35 g, 1.18 g, 2.23 g, 2.89 g, 6.13 g, 1.28 g, 3.12 g, 1.21 g, 8.58 g, 2.34 g, 7.42 g, 4.43 g, 6.36 g, 1.29 g, 4.20 g, 1.11 g, 0.53 g, 0.21 g, and 0.30 g, respectively.

Example 2

A preparation method of an effective part extract of *Monochasma savatieri* included the following steps:
(1) 50 kg of a *Monochasma savatieri* whole herb was pulverized to a length of 3 cm, mixed with 200 L of water, extraction was conducted 4 times by decoction for 40 min each time, filtrates were combined, and vacuum concentration was conducted on a combined filtrate to obtain an extract, namely of a *Monochasma savatieri* crude extract;
(2) the *Monochasma savatieri* crude extract was separated by an HP-20 macroporous resin column chromatography, and eluted with 150 L of each of water and 60% ethanol in sequence, to obtain the LRCW-A and the LRCW-B, respectively;
(3) the LRCW-B was separated by an MCI column chromatography, and eluted with 35 L of each of water, 25% ethanol, 60% ethanol, and 80% ethanol, to obtain LRCW-B1, LRCW-B2, LRCW-B3, and LRCW-B4, respectively;
(4) the LRCW-B2 was separated by a Sephadex LH-20 gel column chromatography, and gradient elution was conducted with absolute ethanol and water in a volume ratio of 1:0 to 0:1 as a mobile phase; and same fractions were combined according to results of thin layer chromatography to obtain the B2-1 to the B2-19; and
(5) the B2-16 was separated by the Sephadex LH-20 gel column chromatography, and gradient elution was conducted with absolute ethanol and water in a volume ratio of 1:0 to 0:1 as a mobile phase; and same fractions were combined according to results of thin layer chromatography to obtain the B2-16-1 to the B2-16-22.

Example 3

A preparation method of an effective part extract of *Monochasma savatieri* included the following steps:
(1) 50 kg of a *Monochasma savatieri* whole herb was pulverized to a length of 5 cm, mixed with 400 L of water, extraction was conducted 2 times by decoction for 20 min each time, filtrates were combined, and vacuum concentration was conducted on a combined filtrate to obtain an extract, namely of a *Monochasma savatieri* crude extract;
(2) the *Monochasma savatieri* crude extract was separated by an HP-20 macroporous resin column chromatography, and eluted with 250 L of each of water and 40% ethanol in sequence, to obtain the LRCW-A and the LRCW-B, respectively;
(3) the LRCW-B was separated by an MCI column chromatography, and eluted with 45 L of each of water, 35% ethanol, 40% ethanol, and 90% ethanol, to obtain LRCW-B1, LRCW-B2, LRCW-B3, and LRCW-B4, respectively;
(4) the LRCW-B2 was separated by a Sephadex LH-20 gel column chromatography, and gradient elution was conducted with absolute ethanol and water in a volume ratio of 1:0 to 0:1 as a mobile phase; and same fractions were combined according to results of thin layer chromatography to obtain the B2-1 to the B2-19; and
(5) the B2-16 was separated by the Sephadex LH-20 gel column chromatography, and gradient elution was conducted with absolute ethanol and water in a volume ratio of 1:0 to 0:1 as a mobile phase; and same fractions were combined according to results of thin layer chromatography to obtain the B2-16-1 to the B2-16-22.

Test Example 1

Inhibitory Effect of TNF-α Secretion

Inflammatory response is a common pathological process in the body, which is a defense response of the body to exogenous pathogenic factors and an important cause of body damage. A variety of cytokines are involved in the inflammatory response, and TNF-α is one of the most important inflammatory factors and plays an important role in the occurrence and development of various inflammatory diseases.

This test example simulated the inflammatory response at a cellular level in vitro, that is, the inflammatory response of mouse peritoneal macrophages (RAW264.7) was induced by lipopolysaccharide (LPS) to produce models of the inflammatory factors, and an inhibitory effect of the effective part extract of *Monochasma savatieri* on the TNF-α secreted by cells was detected by ELISA, to evaluate an anti-inflammatory effect thereof.

Test reagents were: RAW264.7 cells; a DMEM medium, a 1640 medium (Invitrogen), fetal bovine serum (Gibco); LPS(Sigma); an ELISA kit (ebioscience), and a CCK8 reagent (Taosu, Beijing).

Test samples were: the B2-13, B2-15, B2-16, and B2-16-15 prepared in Example 1; a positive drug: dexamethasone.

Experimental equipment were: a cell scraper; a $CO_2$ incubator (SANYO); a microplate reader (BioTek H1).

Test method:
1. Cell culture: the RAW264.7 cells were cultured in the 1640+10% FBS at 37° C. with 5% $CO_2$, and the cells were passaged when showing logarithmic growth. When reaching 80% confluency, the cells were plated in a 96-well plate (density: $2\times10^4$ cells/well) at 100 μL/well, and then incubated at 37° C. with 5% $CO_2$ for 12 h to 18 h.
2. Experimental design: grouping: 1) a control group: 10% FBS medium; 2) a model group (model): LPS (1 μg/mL); 3) and sample groups (sample): LPS (1 μg/mL), the B2-13, B2-15, B2-16 and B2-16-15 (each at 100 μg/mL), and dexamethasone 10 μM.
3. Experimental steps: (1) the cells were plated in a 96-well plate, and incubated at 37° C. with 5% $CO_2$ for 12 h to 18 h; (2) a supernatant was discarded, a 2% FBS medium was added at 80 μL/well, and then incubated for 4 h; (3) the B2-13, B2-15, B2-16, B2-16-15, and dexamethasone were added at 10 μL/well, and incubated for 1 h; (4) the LPS was added at 10 μL/well, and incubated for 24 h; (5) a supernatant was collected to detect the TNF-α according to instructions of the ELISA kit.

Evaluation index: an inhibition rate of the inflammatory factor TNF-α. OD values were read at 450 nm and 570 nm, a standard curve was plotted, a concentration of TNF-α in the medium was calculated, and the inhibition rate and inhibitory activity $IC_{50}$ value of the samples on the TNF-α produced by the cells were calculated.

TNF-α inhibition rate (%)=$(C_{model}-C_{sample})/C_{model}\times$ 100%, where C was an absolute concentration of the TNF-α, and TNF-α in the model group had an absolute concentration of 12.857 ng/mL.

Table 1 shows an effect of the effective part extract of *Monochasma savatieri* on the TNF-α.

TABLE 1

Effect of effective part extract of *Monochasma savatieri* on TNF-α

| No. | Concentration | TNF-α inhibition rate (%) |
|---|---|---|
| B2-13 | 100 μg/mL | 81.60 |
| B2-15 | 100 μg/mL | 71.72 |
| B2-16 | 100 μg/mL | 71.57 |
| B2-16-15 | 100 μg/mL | 59.04 |
| Dexamethasone | 10 μM | 58.67 |

The results in Table 1 showed that compared with the positive drug control group, the inhibition rates of B2-13, B2-15, B2-16, and B2-16-15 were 81.60%, 71.72%, 71.57% and 59.04%, respectively; at the concentration of 10 μM, the positive drug dexamethasone inhibited the production of TNF-α by 58.67%. Therefore, the B2-13, B2-15, B2-16, and B2-16-15 each had an obvious inhibitory effect on the production of inflammatory factor TNF-α.

In order to further clarify an inhibitory strength of the B2-13, B2-15, B2-16, and B2-16-on the production of TNF-α by macrophages (RAW264.7), 5 concentrations were set to calculate the $IC_{50}$ values of B2-13, B2-15, B2-16, and B2-16-15 for inhibiting the TNF-α. The results were shown in Table 2.

TABLE 2

Intensity of effect of B2-13, B2-15, B2-16, and B2-16-15 on inhibition of TNF-α production by macrophages RAW264.7

| No. | TNF-α inhibition rate (%) | | | | | $IC_{50}$ |
| | 100 μg/mL | 50 μg/mL | 15 μg/mL | 5 μg/mL | 1.5 μg/mL | μg/mL |
|---|---|---|---|---|---|---|
| B2-13 | 86.19 ± 3.03 | 56.64 ± 8.3 | 0.58 ± 8.27 | 3.71 ± 17.48 | 26.37 ± 17.39 | 46.58 |
| B2-15 | 85.43 ± 0.91 | 40.15 ± 4.34 | 11.01 ± 2.87 | 9 ± 3.06 | 36.44 ± 4.9 | 55.60 |
| B2-16 | 89.87 ± 0.84 | 50.62 ± 5.12 | 6.19 ± 4.57 | 12.29 ± 2.05 | 28.86 ± 7.2 | 48.56 |
| B2-16-15 | 88.89 ± 7.78 | 59.04 ± 6.42 | 20.01 ± 15.31 | 21.46 ± 22.79 | 29.61 ± 22.18 | 33.04 |

The results in Table 2 showed that the $IC_{50}$ values of B2-13, B2-15, B2-16, and B2-16-15 for inhibiting TNF-α were 46.58 μg/mL, 55.60 μg/mL, 48.56 μg/mL, and 33.04 μg/mL, respectively.

Test Example 2

In this test example, lung cancer cell line A549 and breast cancer cell line MCF-7 were selected to evaluate an inhibitory effect of the effective part extract of *Monochasma savatieri* on tumor cell proliferation.

Test method: A549 and MCF-7 cells were incubated with DMEM+10% FBS at 37° C. with 5% $CO_2$, and the cells were passaged when showing logarithmic growth. When reaching 80% confluency, the cells were plated in a 96-well plate (density: $4\times10^3$ cells/well) at 100 μL/well, and then incubated at 37° C. with 5% $CO_2$ for 12 h to 18 h; a supernatant was added, a DMEM complete medium was added at 90 μL/well, a tested compound was added at 10 μL/well, and then incubated for 72 h. A supernatant was discarded, a PBS containing a 10% CCK8 reagent was added at 100 μL/well, incubated for 1 h, and an OD value was read at 450 nm.

Grouping: a control group: a medium with 10% FBS; sample groups: the LRCW-A, LRCW-B1 to LRCW-B4, B2-1 to B2-19, and B2-16-1 to B2-16-22 prepared in Example 1.

Evaluation index: an inhibition rate of tumor cell proliferation. The OD value was read at 450 nm, and the inhibition rate of tumor cell proliferation was calculated.

Tumor proliferation inhibition rate (%)=($A_{control}$−$A_{sample}$)/$A_{control}$×100%, where A was the OD value.

The results were shown in Table 3.

TABLE 3

Anti-tumor effect of effective part extract of *Monochasma savatieri*

| | | Inhibition rate of tumor cell proliferation (%) | |
|---|---|---|---|
| Sample ID | Concentration | A549 | MCF-7 |
| LRCW-A | 100 μg/mL | 0 | 82.61 |
| LRCW-B1 | 100 μg/mL | 0 | 45.61 |
| LRCW-B2 | 100 μg/mL | 0 | 82.77 |
| LRCW-B3 | 100 μg/mL | 0 | 75.97 |
| LRCW-B4 | 100 μg/mL | 0 | 70.59 |
| B2-2 | 100 μg/mL | 50.87 | 39.76 |
| B2-3 | 100 μg/mL | 46.24 | 79.29 |
| B2-6 | 100 μg/mL | 25.38 | 64.74 |
| B2-10 | 100 μg/mL | 0 | 61.26 |
| B2-11 | 100 μg/mL | 0 | 84.66 |
| B2-12 | 100 μg/mL | 0 | 84.98 |
| B2-13 | 100 μg/mL | 0 | 79.60 |
| B2-14 | 100 μg/mL | 0 | 76.28 |
| B2-15 | 100 μg/mL | 0 | 78.65 |
| B2-16 | 100 μg/mL | 0 | 55.89 |
| B2-17 | 100 μg/mL | 0 | 80.24 |
| B2-18 | 100 μg/mL | 0 | 72.96 |
| B2-16-1 | 100 μg/mL | 60.76 | 80.08 |
| B2-16-3 | 100 μg/mL | 64.31 | 81.50 |
| B2-16-4 | 100 μg/mL | 56.43 | 83.08 |
| B2-16-5 | 100 μg/mL | 0 | 81.82 |
| B2-16-6 | 100 μg/mL | 0 | 58.10 |
| B2-16-18 | 100 μg/mL | 0 | 67.90 |
| B2-16-19 | 100 μg/mL | 0 | 78.65 |
| B2-16-20 | 100 μg/mL | 0 | 80.24 |
| B2-16-21 | 100 μg/mL | 0 | 79.29 |
| B2-16-22 | 100 μg/mL | 0 | 80.08 |

The results in Table 3 showed that compared with the control group, the 28 fractions: LRCW-A, LRCW-B1 to LRCW-B4, B2-3, B2-6, B2-10 to B2-18, B2-16-1, B2-16-3 to B2-16-6, and B2-16-18 to B2-16-22 had an obvious inhibitory effect on the proliferation of breast cancer cell MCF-7; the 6 fractions: B2-2, B2-3, B2-6, B2-16-1, B2-16-3, and B2-16-4 had an obvious inhibitory effect on the proliferation of lung cancer cell A549. However, the fractions B2-1, B2-4, B2-5, B2-7, B2-8, B2-9, B2-19, B2-16-2, and B2-16-7 to B2-16-17 each had no inhibitory effect on the proliferation of breast cancer cell MCF-7 and lung cancer cell A549.

The above descriptions are merely preferred implementations of the present disclosure. It should be noted that a person of ordinary skill in the art may further make several improvements and modifications without departing from the principle of the present disclosure, but such improvements and modifications should be deemed as falling within the protection scope of the present disclosure.

What is claimed is:

1. A method for treating an inflammatory disease, comprising contacting inflamed tissue with a drug comprising an effective amount of an effective part of *Monochasma savatieri* extract, wherein the effective part of *Monochasma savatieri* extract consists of fraction B2-13, fraction B2-15, fraction B2-16, and fraction B2-16-15;

wherein fraction B2-13, fraction B2-15, fraction B2-16, and fraction B2-16-15 are obtained by the following process:

(1) pulverizing *Monochasma savatieri* to obtain *Monochasma savatieri* powder, mixing the *Monochasma savatieri* powder with water, conducting extraction 2 to 4 times by decoction for 20 min to 40 min each time, combining filtrates, and conducting vacuum concentration on a combined filtrate to obtain the *Monochasma savatieri* crude extract; wherein water is added in a volume to mass ratio of 4 L water/1 kg of *Monochasma savatieri* powder; and extraction by decoction is conducted at about 100° C.;

(2) separating the *Monochasma savatieri* crude extract by an HP-20 macroporous resin column chromatography, and conducting elution with 150 L to 250 L of water and 150 L to 250 L of 40% to 60% ethanol in sequence, to obtain fraction LRCW-A and fraction LRCW-B, respectively;

(3) separating the fraction LRCW-B by an MCI column chromatography, and conducting elution with 35 L to 45 L of water, 35 L to 45 L of 25% to 35% ethanol, 35 L to 45 L of 40% to 60% ethanol, and 35 L to 45 L of 80% to 95% ethanol, to obtain fraction LRCW-B1, fraction LRCW-B2, fraction LRCW-B3, and fraction LRCW-B4, respectively;

(4) separating the fraction LRCW-B2 by a cross-linked dextrin gel LH-20 gel column chromatography, and conducting gradient elution with absolute ethanol and water in a volume ratio of 1:0 to 0:1 as a mobile phase; and combining same fractions having a same $R_f$ value according to results of thin layer chromatography to obtain fraction B2-1, fraction B2-2, fraction B2-3, fraction B2-4, fraction B2-5, fraction B2-6, fraction B2-7, fraction B2-8, fraction B2-9, fraction B2-10, fraction B2-11, fraction B2-12, fraction B2-13, fraction B2-14, fraction B2-15, fraction B2-16, fraction B2-17, fraction B2-18, and fraction B2-19; and (5) separating the fraction B2-16 by the cross-linked dextrin gel LH-20 gel column chromatography, and conducting gradient elution with absolute ethanol and water in a volume ratio of 1:0 to 0:1 as a mobile phase; and combining same fractions according to results of thin layer chromatography to obtain fraction B2-16-1, fraction B2-16-2, fraction B2-16-3, fraction B2-16-4, fraction B2-16-5, fraction B2-16-6, fraction B2-16-7, fraction B2-16-8, fraction B2-16-9, fraction B2-16-10, fraction B2-16-11, fraction B2-16-12, fraction B2-16-13, fraction B2-16-14, fraction B2-16-15, fraction B2-16-16, fraction B2-16-17, fraction B2-16-18, fraction B2-16-19, fraction B2-16-20, fraction B2-16-21, and fraction B2-16-22 wherein the inflammatory disease is caused by secretion of an inflammatory factor TNF-α.

2. The method according to claim 1, wherein the inflammatory disease comprises sepsis, inflammatory bowel disease, rheumatoid arthritis, ankylosing spondylitis, or psoriasis.

3. The method according to claim 1, wherein the drug further comprises a pharmaceutically acceptable carrier or auxiliary material.

* * * * *